United States Patent [19]

Hansen et al.

[11] Patent Number: 5,589,401
[45] Date of Patent: Dec. 31, 1996

[54] LIGHT SCATTER-BASED IMMUNOASSAY WITHOUT PARTICLE SELF AGGREGATION

[76] Inventors: W. Peter Hansen, 20 E. 35th St., Apt. 7G, New York, N.Y. 10016; Michael Cennerazzo, 9 Oak St., Weehauken, N.J. 07087

[21] Appl. No.: 286,778

[22] Filed: Aug. 5, 1994

Related U.S. Application Data

[63] Continuation of Ser. No. 994,903, Dec. 22, 1992, abandoned.

[51] Int. Cl.⁶ .................. G01N 33/538; G01N 33/544; G01N 33/553
[52] U.S. Cl. .................. 436/525; 436/533; 436/541; 436/164; 435/7.1
[58] Field of Search .................. 436/525, 533, 436/541, 164; 435/7.1

[56] References Cited

U.S. PATENT DOCUMENTS

| | | | |
|---|---|---|---|
| 3,873,204 | 3/1975 | Friedman et al. | 356/39 |
| 4,305,925 | 12/1981 | Kapmeyer et al. | 436/509 |
| 4,313,734 | 2/1982 | Leuvering | 436/525 |
| 4,446,239 | 5/1984 | Tsuji et al. | 436/532 |
| 4,480,042 | 10/1984 | Craig et al. | 436/533 |
| 4,581,334 | 4/1986 | Kirchanski | 435/29 |
| 4,853,335 | 8/1989 | Olsen et al. | 436/527 |
| 5,017,009 | 5/1991 | Schutt et al. | 356/338 |
| 5,079,172 | 1/1992 | Hari et al. | 436/518 |
| 5,162,863 | 11/1992 | Ito | 356/73 |
| 5,286,452 | 2/1994 | Hansen | 422/73 |

FOREIGN PATENT DOCUMENTS

| | | |
|---|---|---|
| 0258963 | 9/1988 | European Pat. Off. . |
| 0426300 | 9/1990 | European Pat. Off. . |
| 8906801 | 7/1989 | WIPO . |

OTHER PUBLICATIONS

H. Bauer, et al. *Experientia*, 31:1149–1151 (1975).
M. Horisberger, et al. *J. of Histochem. and Cytochem.*, 25(No. 4): 295–305 (1977).
M. Horisberger. *Biol. Cellularie*, 36:253–258 (1979).
Sakai et al., *Chem. Pharm. Bull.* 37(11):3010–14 (1989).
J. H. W. Leuvering et al., *J. of Immunological Methods*, 62:163–74 (1983).
J. H. W. Leuvering et al., *J. of Immunological Methods*, 45:183–94 (1981).
F. Wielaard et al., *J. of Virological Methods*, 17:149–158 (1987).
Duke Scientific Corporation Bulletin 88C Sep. 1, 1990 "Covaspheres Reagants".
Duke Scientific Corporation Bulletin 93D Apr. 1, 1992 "Flourescent Microspheres & Particles".
Horisberger et al., *Experientia*, 31:1147–9 (1975).
Rohr et al., *Analytical Biochemistry*, 182, 388–398 (1989).
Saunders, G. C. et al., Clinical Chemistry 31(12):2020–2023 (1985).
Van Erp et al., *J. Immunoassay*, 12:425–443 (1991).
Odell et al., *Principles of Competitive Protein–Binding Assays*, ed. 13:243–254 (1983).

*Primary Examiner*—James C. Housel
*Assistant Examiner*—Nancy J. Parsons
*Attorney, Agent, or Firm*—Lerner, David, Littenberg, Krumholz & Mentlik

[57] ABSTRACT

A homogeneous immunoassay method for the simultaneous determination of one or more antibody, antigen or hapten analytes in a fluid sample, that comprises the quantification of the effect of said analytes on the statistical changes in a dimension of a light scatter pulse height distribution histogram of relatively large diameter monodisperse binding molecule-coated polymeric microspheres induced by the binding to said microspheres of polydisperse binding molecule-coated colloid metal particles of relatively small diameter. For simultaneous assays of multiple analytes, different diameter or refractive index microspheres are assigned to each analyte. The assay may be used in forward binding, displacement, inhibition, and competition type systems, with the direction of the change in histogram dimension depending on the system. A convenient dimension to measure is the normalized peak width of a graphical representation of the histogram. For simultaneous assays for multiple analytes, a monodisperse polymeric microsphere of unique diameter or refractive index is dedicated to each analyte, so as to generate multiple histograms, one for each analyte. Polydisperse binding molecule-coated colloid metal particles, when used in effective concentrations, will also serve as a scavenger means to reduce the interfering effects of non-specific substances in the analyte-containing fluid samples, particularly when said samples are of biological origin.

36 Claims, 10 Drawing Sheets

POLYSTYRENE SPHERE (MONONISPERSED IN SIZE) APPROX 1 MICRON DIAMETER

● COLLOIDAL METAL PARTICLE (POLYDISPERSED IN SIZE APPROX 20 nm TO 120nm DIAMETER)

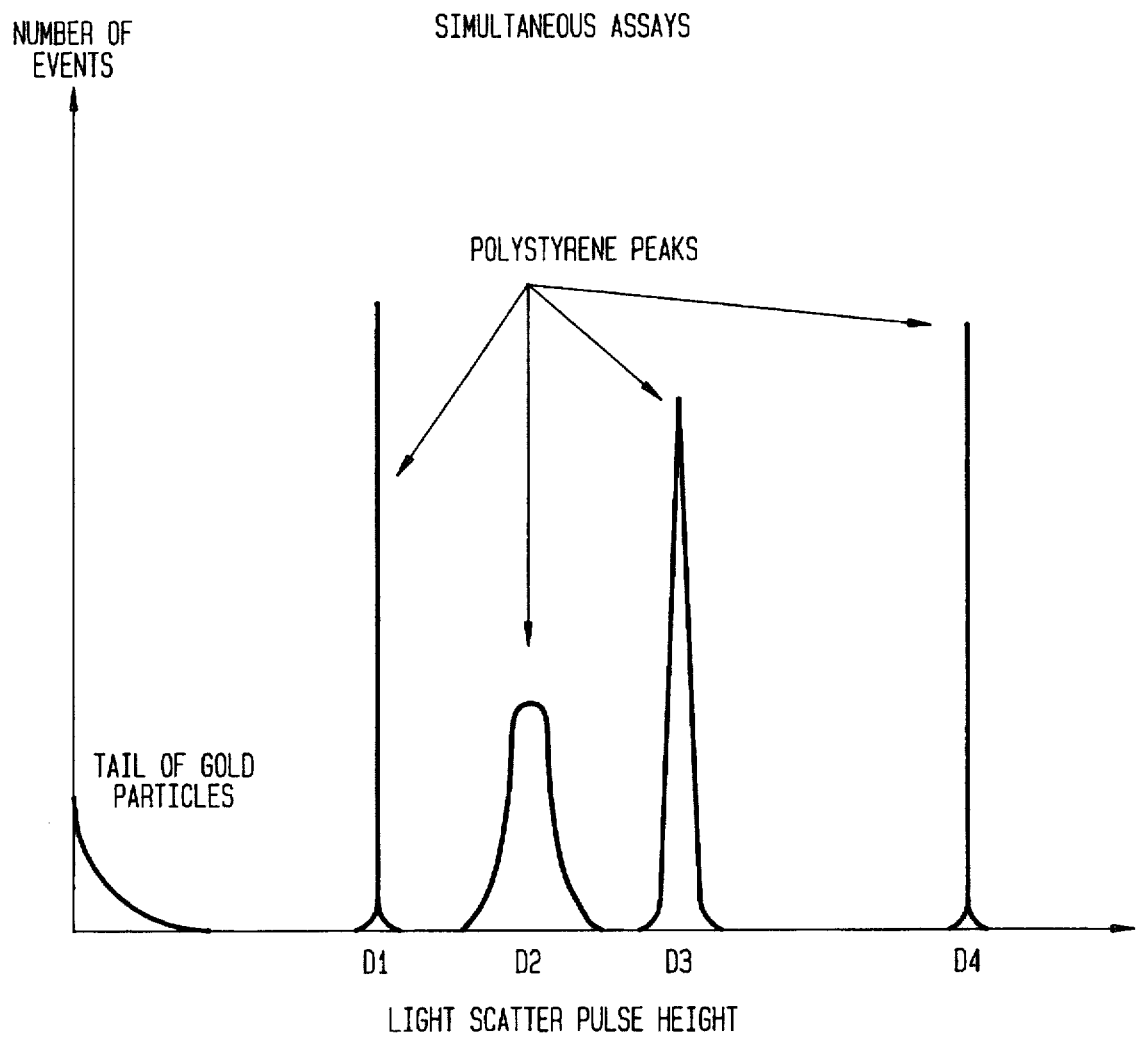

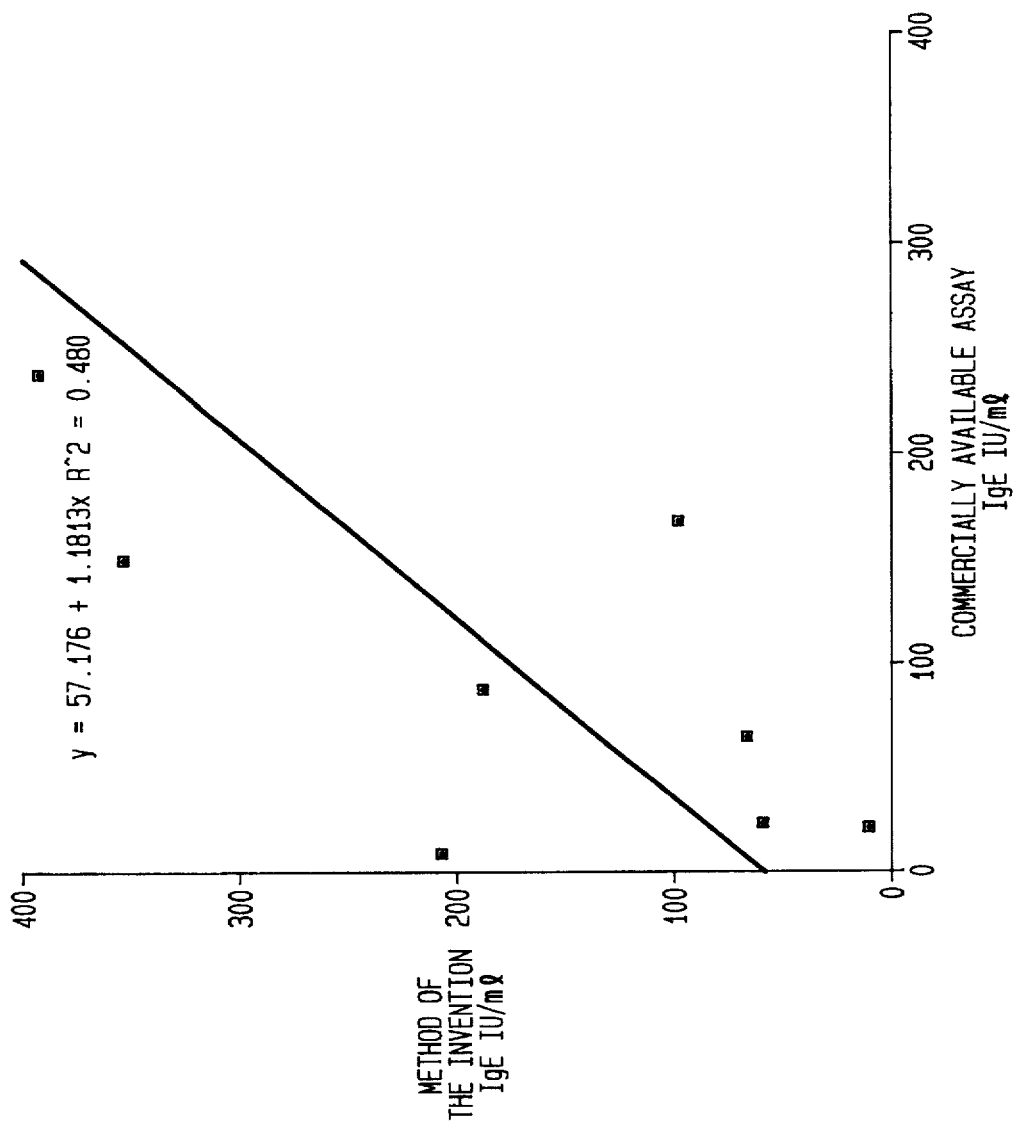

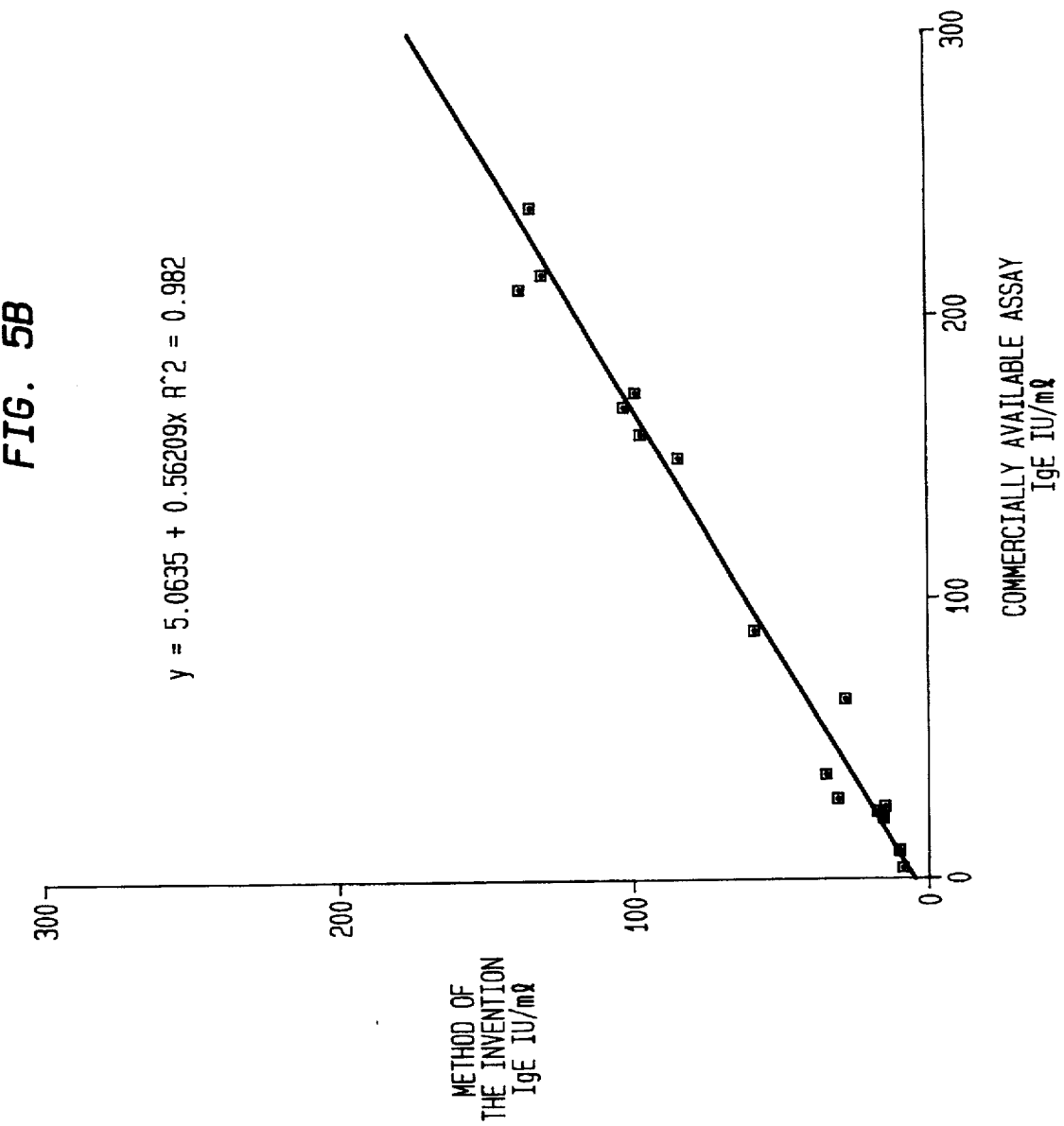

LIGHT SCATTER-BASED IMMUNOASSAY WITHOUT PARTICLE SELF AGGREGATION

This is a continuation of application Ser. No. 07/994,903, filed on Dec. 22, 1992, now abandoned.

BACKGROUND OF THE INVENTION

1. Field of the Invention

The invention relates broadly to homogeneous immunoassay methods for measuring an antigen, antibody or hapten analyte in a fluid sample by measuring light scatter signals from monodisperse particles in a flow particle analyzer. More particularly, the invention relates to measuring changes in light scatter signals from binding molecule-coated monodisperse polymeric microspheres as the result of the analyte-mediated binding to such microspheres of binding molecule-coated polydisperse colloidal metal particles.

2. Description of the Prior Art

Antibodies, antigens and many haptens exhibit high affinities, not only for their complementary proteins, but also for certain solid surfaces such as those found in the wells of plastic microtiter plates, walls of plastic test tubes, polymeric microspheres, and colloidal metal particles. Exploitation of these properties has led to a revolution in the field of diagnostic assay methods for the aforementioned analytes in fluid samples such as serum.

The ability to carry out antigen-antibody interactions on solid supports has greatly simplified the separation of analyte-containing immunocomplexes from unused reactants and interfering substances, such as those often present in biological fluids. Such systems are generally referred to as "solid phase immunoassays" or "immunosorbent assays", and fall within the genus of "heterogeneous immunoassays." While the phase separation steps in heterogeneous immunoassays are valuable in reducing interferences by nonspecific binding substances that generally have an adverse effect on the sensitivity of the assay method, such assays are cumbersome and expensive, and are a focal point for reliability problems in automated systems.

Additionally, such heterogeneous systems have the additional disadvantage of requiring that one or another member of the immunocomplex be labeled with a molecule that can be easily quantified. Such molecules are generally referred to as "reporter molecules" and include radioisotopes (radioimmunoassays, RIA), enzymes (enzyme-linked immunoassays generally coupled with a chromophore, ELISA), fluorescent molecules (fluorescence immunoassays, FIA), chemiluminescent molecules (CIA), gold particles, photosensitive molecules, and the like. For a review, see Kemeny, D. M., et al., Immunology Today, 7: 67 (1986). Further, because of the limited number of chromophores and fluorophores available as receptor molecules, and the extensive overlap of emission spectra of such molecules, simultaneous assay of multiple analytes are not suitable using these reporters. For example, Cambridge Biotech's simultaneous EIA assays for *C. difficile* Toxin A and Toxin B, HTLV-I and HTLV-II, and HIV-1 and HIV-2, are not separable. The present invention greatly simplifies separability of signals from multiple analytes in a single reaction mixture.

"Homogeneous immunoassay" is the term applied to immunoassays in which no phase separation occurs. Such systems, which include binding protein-coated particle agglutination assays, are useful because they have fewer steps to automate, and automation is mechanically, fluidically and electrically simple. Examples of immunoassays requiring no phase separation steps include: latex microsphere agglutination, hemagglutination, and fluorescence depolarization assays. Examples of latex bead agglutination assays for single analytes are found in U.S. Pat. Nos. 4,521,521, 4,184,849, 4,279,617, 4,191,739 and 4,851,329, and for multiple analytes in a single fluid sample in Hansen, U.S. Pat. No. 5,286,452. Nephelometric or turbidimetric automated systems for agglutination or fluorescence depolarization assays are simple, inexpensive to construct, and, unlike heterogeneous assays, do not require frequent maintenance of the complicated phase separation apparatus.

The presence of interfering substances in body fluids has, however, inhibited otherwise promising homogeneous immunoassay approaches from meeting the high sensitivity requirements of many medically important tests, such as are met by ELISA and RIA. For reviews of this problem see, for example, Masson et al., *Methods in Enzymology*, 74: 115(1981) and Collett-Casssart et al., *Clin Chem.*, 27:64 (1981). One important aspect of the present invention is that it is a homogeneous immunoassay that is free from non-specific interferences, at least to a sensitivity level of about $5 \times 10^{-13}$M. This level of sensitivity is two to three orders of magnitude greater than prior art homogeneous latex bead agglutination assays. See, e.g., alpha-fetoprotein ($3 \times 10^{-10}$M, Collett-Cassart et al. above), urinary HCG ($6 \times 10^{-11}$M, Lentrichia et al., *J. Immunol. Meth.*, 89:657(1986) (but exhibiting only an 87% correlation with RIA at analyte levels 20 times the claimed sensitivity limit), and serum digoxin by a fluorescence depolarization method ($3 \times 10^{-10}$M, S. Wong in D. Chan, ed., *Immunoassay Automation*, Academic Press, 1992, p. 329).

Prior art approaches to eliminating or decreasing the undesirable effects of non-specific interfering substance on homogeneous immunoassays have been generally unsatisfactory. These include: high dilution of body fluid sample (Fritz et al., *J. Immunol.*, 108:110(1972), but this proportionally decreases sensitivity; using antibody fragments (Masson, Id.), but this approach is expensive and unpredictable; and, use of special conditions of pH, ionic strength, and buffer type, and/or addition of chelators or other scavengers (Masson, Id.), but these introduce multiple dependent factors that must be optimized for each analyte, and can become prohibitively expensive and cumbersome (Lim et al., *J. Clin. Chem. Clin. Biochem.*, 20:141(1982).

Other approaches to solving the non-specific interference problem have included using IgG-coated latex ultramicrospheres to inhibit non-specific reactions in a latex sphere agglutination assay that uses antibody fragments. The sensitivity of one such agglutination method using a Coulter principle electronic resistance flow particle analyzer with a 30 μm orifice was reported to be about $5 \times 10^{-13}$ to $4 \times 10^{-12}$M. Sakai et al., *Chem. Pharm. Bull.*, 37:3010 (1989). The disadvantages of this approach is that the additional reagent (non-specific, IgG coated ultramicrospheres) has an incremental manufacturing, quality control and storage cost associated with it. The present invention removes this important disadvantage by combining the action of specific immunoreactivity with the action of improving specificity, all in one reagent. In addition, although the Coulter principle particle counter used by Sakai et al. yields quantitative results, the need for the small (30 μm) orifice in order to sense agglutination has the well known problem of clogging during agglutination reactions (Masson, Id.). The present invention uses a sheath flow particle analyzer with a 250–300 μm orifice, which eliminates clogging. However, in the Sakai et al. approach, the distribution of specifically agglutinated particles (dimers, trimers, etc) presents a problem in Coulter volume overlap if simultaneous assays of more than one analyte are attempted, a problem not encountered in the present invention as multimers are not formed and multiple simultaneous assays can be performed without algorithms to remove the problem of overlap.

Another problem encountered in prior art agglutination immunoassays is the need for agitation by mechanical mixers during the entire reaction period of reaction mixtures containing particles of one micron or greater (Masson, Id.), thus requiring stringent washing between samples to prevent carryover of samples. A further advantage of the present invention, insofar as automation is concerned, is that agitation of samples is not needed to complete the agglutination reaction during useful time frames.

Schutt et al., EP 0254430 and U.S. Pat. No. 5,017,009, show a scattered total internal reflectance (STIR) assay method for an analyte in which colloidal gold particles are used as a label for proteins that bind to a coated macroscopic plastic plate of optical quality. This immunoassay relies upon the detection of back scattered light from an evanescent wave disturbed by the presence of a colloidal gold label brought to the interface by an immunological reaction. This evanescent wave is said to be the result of a totally internally reflected incident light wave. A disadvantage of this system is that the expensive optical-quality plastic plate is not reusable and must be discarded after a single use.

There remains an important need for an immunoassay method for antigens, antibodies, and haptens in fluid samples that combines the mechanical simplicity and low cost of particle agglutination homogeneous assays with the reduction in deleterious effects of interfering substances enjoyed by solid support based heterogeneous assays, and that does so with increased efficiency and scope when compared to prior art agglutination assays. This need is now fulfilled by the invention described in detail below.

SUMMARY OF THE INVENTION

The invention relates to a novel immunoassay method for simultaneously detecting and quantifying the concentration in a single fluid sample of one or more antigen, hapten or antibody analytes. The invention is based upon the serendipitous and unexpected observation that the binding of relatively small polydisperse binding molecule-coated colloidal metal particles to the surface of relatively large monodisperse binding molecule-coated polymeric microspheres produces changes in the dimensions of light scatter pulse height distribution histograms of these polymeric microspheres, and that these changes in histogram dimension can be correlated with the concentration of the analyte that induces the dimension changes. Preferred light scatter is substantially low angle forward light scatter or substantially right angle light scatter. A convenient histogram dimension to determine for this purpose is the normalized peak width of a graphical representation of the histogram, that is, the peak width at one-half peak height.

In a forward binding reaction (sandwich) embodiment, a monodisperse immunocomplex is formed between large monodisperse polymeric microspheres coated with a first binding molecule, small polydisperse colloid metal particles coated with a second binding molecule, and an analyte that is complementary to both binding molecules. The dimensions of the light scatter pulse height distribution histogram of the monodisperse particulate immunocomplex are compared with control histogram dimensions (obtained with monodisperse coated polymeric microspheres in the absence of metal particles and linking analyte tested before, after, on during the analytical run), and the statistical increases in histogram dimension due to the presence of the analyte are correlated with the concentration of the analyte in the fluid sample. In a displacement embodiment of the invention, an immunocomplex reagent is first formed between monodisperse polymeric microspheres coated with the analyte and polydisperse colloidal metal particles coated with an anti-analyte antibody, the light scatter histogram dimensions of the immunocomplex is determined before and after its exposure to the analyte, and the statistical changes of the histogram dimension after exposure to the analyte correlated with analyte concentration in the fluid sample. In a competition embodiment of the invention, an analyte competes against anti-analyte antibody-coated polydisperse colloidal metal particles for binding to monodisperse polymeric microspheres coated with a first binding molecule complementary to the anti-analyte antibody. A reduction by analyte in the extent of immunocomplex formation between the microspheres and metal particle, reduces a dimension of the light scatter pulse height distribution histograms in proportion to the concentration of analyte in the fluid sample. In an inhibition reaction embodiment, the immunoassay relies upon the ability of analyte to inhibit the binding of anti-analyte-coated polydisperse metal particles to binding molecule-coated monodisperse polymeric microspheres.

In one aspect of this invention, there are disclosed details and scope of forward binding, displacement, competition and inhibition embodiments of the aforementioned inventive method.

In another aspect there are disclosed polymeric microspheres and colloid metal particles suitable for carrying out the method of the invention.

In still another aspect there are disclosed examples of the application of the inventive method to the estimation of specific analytes in biological fluid.

It is yet another aspect of the invention to disclose application of the inventive method to the simultaneous assay of multiple analytes in the same fluid sample in a single analytical run.

It is yet another object to disclose the concurrent use of coated metal particles, not only for analytical purposes, but also as scavengers that advantageously remove interfering non-specific substances present in biological samples from immunoassay reaction mixtures.

These and other objects will become apparent by reference to the following detailed description of the preferred embodiments and the appended claims.

DESCRIPTION OF THE DRAWINGS

FIG. 1D illustrates a light scatter pulse height histogram for a simultaneous multiple-analyte assay.

FIGS. 5A and 5B show a latex-latex agglutination assay correlation curves for IgE.

DETAILED DESCRIPTION OF THE PREFERRED EMBODIMENTS

Figure 1A:
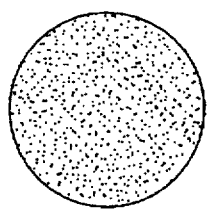
FIG. 1A shows polymeric microspheres and metal particles.

The invention relates to novel immunoassay methods for antigen, antibody and hapten analytes in a fluid sample based on flow particle analysis. The methods take advantage of the serendipitous and unexpected discovery that a statistical change occurs in measured values of certain physical properties of a preparation of relatively large monodisperse polymeric microspheres when relatively small polydisperse metal particles bind to the former microspheres in an immunochemical reaction induced, proportionally to concentration, by an analyte. Examples of particle properties that can be monodispersed, as measured by flow particle analyzers, are: the so-called Coulter-volume of insulating particles in a given orifice diameter in an electrical impedance flow particle analyzer; the fluorescent emission by single particles when illuminated at a given wavelength, also in an optical flow particle analyzer; and, the light scatter pulse height distribution histogram of monodisperse microspheres substantially in a given direction when illuminated in an optical flow particle analyzer. The last-named property is used in the present novel method for concurrently measuring one or more antigen, antibody, or hapten analyte in a single fluid sample, a method that is also capable of avoiding or reducing the deleterious interfering effects of non-specific substances in biological fluid samples, in prior art agglutination immunoassays.

The optical flow particle analyzer (FPA) used in the invention uses a sheath flow cell through which passes a guided narrow sample stream, and light scatter, preferably substantially low angle forward light scatter or substantially right angle light scatter, of an incident light beam, preferably a laser beam, to sense and measure the degree of immunochemically-induced complex formation between relatively small polydisperse colloidal metal particles and a population of relatively large monodisperse polymeric microspheres. The method is based upon the unexpected discovery that the aforementioned polydisperse metal particles, which themselves do not scatter light under the conditions of the invention in the region of the polymeric particles (even after the former are agglutinated by virtue of reaction with nonspecific binding components found often in sera), cause profound changes in the light scatter pulse height distribution histogram dimensions of the monodisperse polymeric microspheres when the metal particles bind to the surface of the polymeric microspheres to form an immunocomplex. Where the polymeric microspheres are coated with a first complementary binding molecule and the metal particles with another, a protein (i.e., antigen or antibody) or hapten analyte that is complementary to both first and second binding molecules will crosslink the metal particles to the polymeric particles, and will bring about a change in the dimensions of the light scatter pulse height distribution histogram of the monodisperse polymeric microspheres compared to the control histogram dimensions obtained in the absence of metal particles and analyte. The aforementioned change in the histogram dimensions has been found to correlate directly with the amount of the analyte present in the fluid sample.

It is an important discovery that the aforementioned change in the histogram dimension occurs in the absence of any significant shift in the position of the monodisperse polymeric microsphere light scatter pulse height distribution histogram, which indicates that self-aggregation of polymeric microspheres is not involved.

Figure 2A:
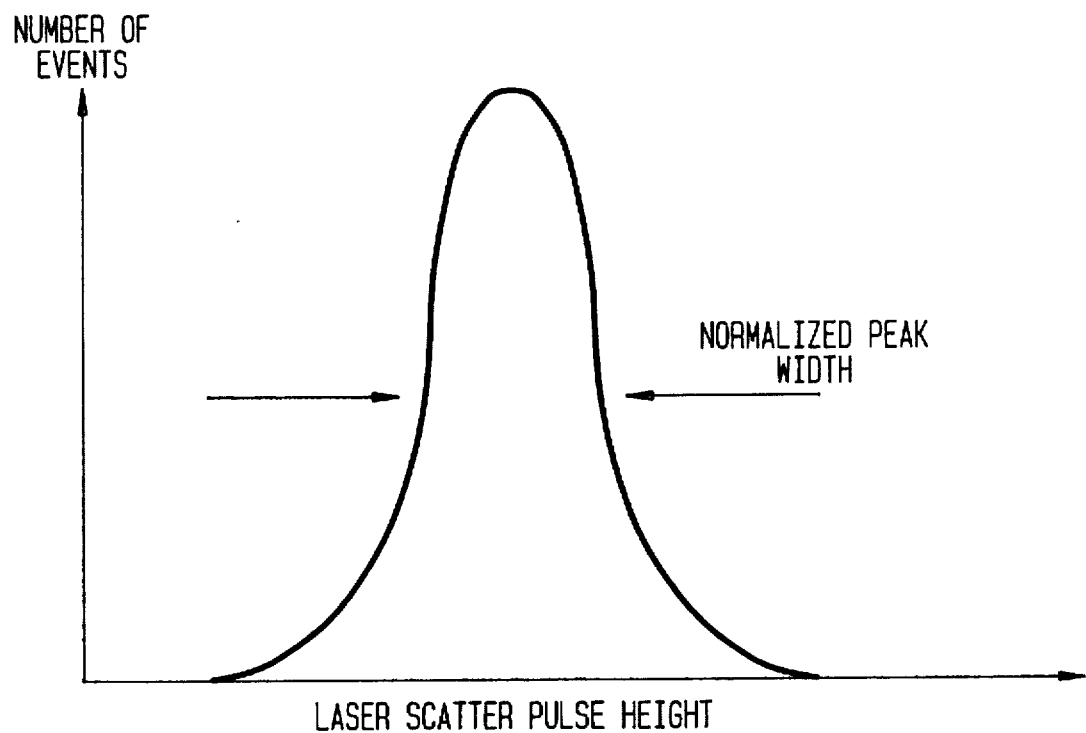
FIGS. 2A and 2B show the normalized peak width parameters and calibration (i.e., standard) curve, respectively, for a forward binding (i.e., sandwich) assay.

The preferred dimension for monitoring changes in the histogram is the peak width at one half peak height of the graphical representation of the light scatter pulse height distribution histogram. This dimension will be referred to in this specification as "normalized peak width" or "NPW" (see FIG. 2A for example). In the forward binding (sandwich) immunocomplex formation method described above, the change in histogram dimension is a widening of the NPW in the graphical representation and, consequently, an increase in the coefficient of variation (CV) around the histogram mean.

It has also been discovered that measurement of statistical changes in the dimension of a light scatter pulse height distribution histogram can be the basis for a quantitative determination of an analyte in a fluid sample in displacement-, competition- and inhibition-type immunoassay methods.

In a displacement embodiment, an immunocomplex reagent is prior-prepared by immunobinding polydisperse colloid metal particles coated with an anti-analyte antibody to monodisperse polymeric microspheres coated with analyte. A base line determination of the light scatter pulse height distribution histogram of this reagent will show a dimension that resembles that which results when the two types of particles are immunocomplexed, that is, a wide NPW if this is the dimension examined. When this reagent is mixed with a solution containing an analyte that is complementary to the binding molecule with which the metal particles are coated, the metal particles will be displaced from the immunocomplex reagent in direct proportion to the concentration of analyte present, and the histogram dimension will return to that resembling control monodisperse polymeric microspheres, that is, the dimensions of the histogram will be reduced, that is to say, the NPW (and CV) will be reduced. The statistical extent of dimension reduction, as reflected in the NPW, can be correlated by standard means to the concentration of analyte in the fluid sample.

In a competition embodiment, binding molecule-coated monodisperse polymeric particles and analyte compete for binding to binding molecule-coated polydisperse metal particles. The NPW for the polymeric particles is inversely related to the concentration of fluid sample being analyzed, that is to say, a high analyte concentration will "capture" a relatively larger fraction of the metal particles, leaving a relatively smaller fraction of metal particles to bind to the polymeric microspheres. This will produce a relatively narrow histogram, that is, a small NPW. As in the previous two embodiments, the analyte may be an antigen, hapten or antibody, and it is well within the skill of the assayist, following the guidelines provided by the invention, to select appropriate binding molecules with which to coat the microspheres and metal particles.

In an inhibition embodiment, the analyte-containing sample is incubated with anti-analyte antibody-coated polydisperse metal particles and incubated for a finite time which does not necessarily include the time necessary to reach equilibrium, which may be on the order of hours. Analyte-coated monodisperse polymeric microspheres are then added and incubation is continued for another finite time, which is of the order of minutes, during which period the analyte inhibits the binding of metal particles to the polymeric microspheres. Histogram dimensions are determined as above. High concentrations of analyte will produce narrow histogram peak widths as the result of its sequestering of the metal particles; low concentrations of analyte will produce the reverse.

As noted above, it is an important feature of the embodiments of the invention that incubation mixtures used need not be stirred during reaction periods. When adding components of reaction mixtures, only brief mixing (1–2 seconds) to produce homogeneity of the mixture is required.

A variety of commercially available polymeric particles may be used in this invention, although highly preferred are uniform latex microspheres. Bangs, L. B., Uniform Latex Particles, Seragen, Ind., 1984. Although the term "latex", strictly speaking, refers to the polyisoprene of which milk sap is composed, the definition of this term has been expanded, and will be used herein to include synthetic polymers such as polybutadiene, polystyrene and the like. Uniform latex microspheres of average diameter-ranging between 0.05 and 10 µm, preferably between about 0.5 and about 5.0 µm, and having stable hydrophobic surface groups to which proteins bind strongly so as to produce stable hydrophilic colloidal suspensions, are preferable diameters for use in the invention, although diameters ranging up to about 100–120 µm are available commercially. The 0.5 to 5.0 µm diameter latex microspheres with highly monodispersed diameters are available from Polysciences, Inc., Warrington, Pa. 18976 and from Interfacial Dynamics Corp., Portland, Oreg. 97220. The standard deviation of diameters expressed as per-cent of the mean (i.e., coefficient of variation, or CV) are approximately 1% to 2% for these commercial preparations, and it is highly preferred that CV's of 2% not be exceeded.

The CV of the light scatter pulse height distribution histogram obtained from these spherical particles is a strong function of the relative diameter of the sample stream through the flow cell of the FPA and the focal dimensions of the incident (e.g., laser) light. If the sample stream is relatively large, then particles can flow through different intensities of the incident light beam and yield an undesirably large CV of pulse heights, even though the CV of the particles themselves is small. Therefore, it is essential that a narrow sample stream of constant dimensions be maintained in order to practice this invention optimally. Means for accomplishing this will be described below.

Although central bore diameters for the optical capillary flow cell ranging between 100 µm and 500 µm are suitable for purposes of the present invention, a central bore diameter of about 250 µm is preferred. It is preferred to center the fluid sample stream and to confine it to a diameter range of about 3 µm to 10 µm. In a highly preferred system, this diameter amounts to about 1% to 3% of the width of the laser light beam. Under these conditions, CV values for light scatter pulse height distribution histograms of less than 2% for monodisperse polymeric microspheres can be obtained, and are most preferred. As used in the present context "monodisperse" is taken to mean a population of polymeric microspheres that produce a low angle forward scattered light pulse height distribution histogram with a CV of no greater than about 2%. When the sample stream diameter is not controlled so as to give a histogram CV of about 2% or less for non-immunochemically sensitized control monodispersed spherical particles, the sensitivity of the method is adversely affected, and the symmetrical broadening or narrowing of the histogram are not readily observed.

A variety of fluid drive means can be used to achieve the aforementioned narrow fluid stream. These include stepped motor controlled syringe pumps and vacuum devices. Persons skilled in this art will recognize that the best mode would be one in which the stream diameter could be either directly or indirectly regulated during a measurement and controlled to the proper dimension range. It is also desireable to provide the flow cell with a stream centering means so as to confine the narrowed fluid sample stream as precisely as possible in the center of the sheath flow. To monitor both the narrowing and centering features, it is possible to monitor the sample stream before, after and during the times during which the immunoreacted particles are measured. This can be accomplished in either case with a control population of monodisperse polymeric microspheres of the same or different diameters as that of the analytical microspheres and that do not participate in any immunobinding reactions. Such control microspheres can serve as a component of a sentinel system that includes an electronic sensing means that senses departures from the desired CV value, and that feedback regulates both or either the stream narrowing means and stream centering means so as to achieve the desired CV value.

As noted above, to carry out the inventive method in the forward binding (sandwich) reaction embodiment, both the relatively large monodisperse microspheres and the relatively small polydispersed metal particles are coated with different complementary binding molecules. Where the analyte is an antigen or hapten, monodisperse polymeric microspheres are coated with a first complementary anti-antigen or hapten analyte antibody, which may be a monoclonal antibody directed to a first epitope on the antigen. The polydisperse metal particles are coated with a second anti-antigen analyte antibody, which may be a monoclonal antibody directed to a second epitope of the antigen analyte. In the presence of antigen, a typical "sandwich" reaction takes place, with the antigen crosslinking the smaller metal particles randomly on the surface of the larger polymeric microspheres. When this occurs, and the resulting particulate immunocomplexes are passed through the optical flow cell described above, we have found unexpectedly that the CV and standard deviation of the monodispersed light scatter pulse height distribution histogram, as reflected in a graphical representation of the histogram, produces peaks that broaden approximately symmetrically about the peak mean. We have also discovered that this broadening is directly and quantitatively related to the concentration of the analyte in the fluid sample.

Figure 1B:
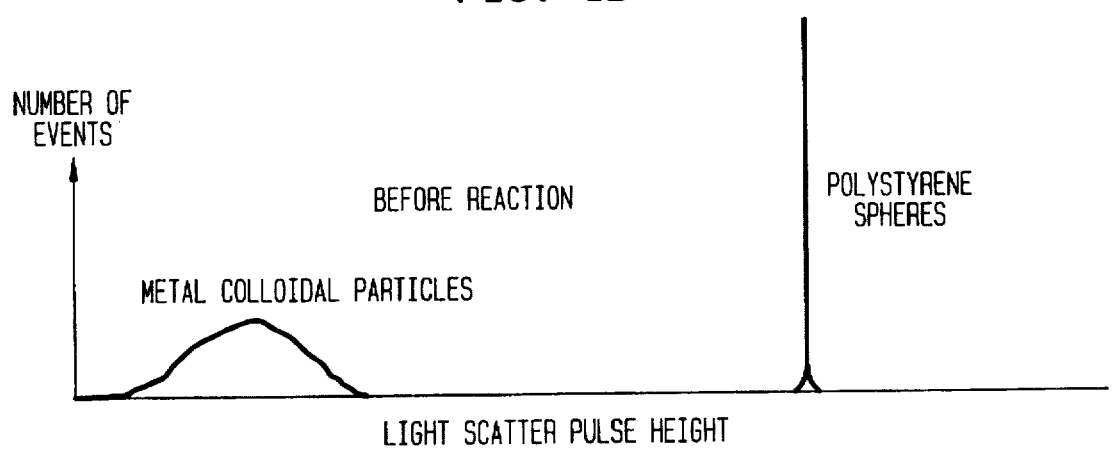
FIGS. 1B and 1C show light scatter pulse height distributions before and after binding of metal particles to monodisperse polymeric particles, respectively.
Figure 1C:
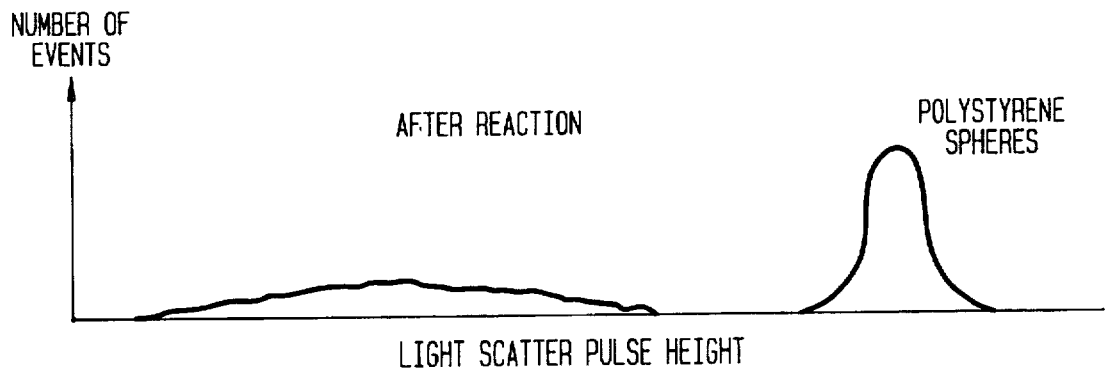

The principle of this embodiment of the invention is shown in FIG. 1. In FIG. 1A are shown the relative diameters of monodisperse latex microspheres (about 1.0 µm diameter) and the polydisperse colloidal metal particles (about 20 to 120 nm in diameter). In the preferred particle diameters described above, it can be seen that the ratio of polymer microsphere diameter to metal particle size ranges between 15–30:1. This characteristic provides the potential for a large number of colloidal metal particles to be bound randomly on each polymeric microsphere. The light scatter pulse height distribution histogram for the latex microspheres is shown in FIG. 1B. The pulse height signal from the latex microspheres is high, and the width of the peak representing the histogram is very narrow. As is evident, the small amount of light scatter from self agglutinated metal particles does not interfere, i.e., does not overlap, with the histogram produced by the microspheres. After analyte-mediated binding of the metal particles to the latex microspheres, a broadening of the latex histogram peak occurs (FIG. 1C) in a forward binding reaction. Even when multiple analytes in a single sample are analyzed simultaneously by a combination of the present embodiments (histograms D1, D2, D3 and D4 in FIG. 1D), there is no overlap with the signal generated by unbound gold particles.

Methods for producing stably adsorbed proteins on latex microsphere surfaces are described generally in Seaman, G. V. F., ed., Latex Based Technology in Diagnostics, Health & Science Communications, Washington, D.C. 20005, 1990, which is incorporated by reference.

We have discovered that this invention may also be carried out in a displacement embodiment. To carry out the invention in this mode, the two types of particles are first immunochemically sensitized by incubation separately with complementary binding molecules to form a two component immunocomplex reagent. In one embodiment, the large polymeric microspheres are coated stably with analyte. The metal particles are coated with a binding molecule that is complementary to the analyte. The two suspensions are mixed to form a reagent that may be stored prior to use. This reagent is then mixed with the analyte-containing fluid sample. The analyte displaces a portion of the bound metal particles from the polymeric microspheres by virtue of immunocomplex formation. This displacement results in a decrease in the dimension of the light scatter pulse height distribution histogram of the aforementioned immunocomplex reagent. This decrease is proportional to the concentration of analyte present in the fluid sample.

In a competition-type embodiment, an analyte and an analyte-coated polymeric microsphere compete for binding to anti-analyte-coated metal particles. After an appropriate incubation period, the suspension is subjected to FPA and histograms determined. A control consists of the coated polymeric particles alone.

As noted above, in an inhibition embodiment, analyte is incubated with anti-analyte binding molecule-coated polydisperse metal particles for a finite period of time, e.g., 5–30 minutes, during which period the analyte binds to and "sequesters" a portion of the metal particles. Unbound metal particles are free to bind to polymermic microspheres coated with a binding molecule (which may be a carrier binding molecule that contains analyte) that are then added and incubated. FPA of control and experimental monodisperse polymeric microspheres after a brief period, e.g., 5–10 minutes, of incubation will reveal the amount of unbound metal particles which, in turn, is inversely related to the concentration of analyte.

While it has been convenient to describe the forward binding (sandwich) reaction, inhibition, displacement and competition embodiments of the invention in terms of an antigenic or hapten analyte and antibody-coated particles, it should be understood that the scope of this invention includes assays in which the analyte is an antibody present in, for example, human serum and the like. In such assays carried out in the forward binding mode, both types of particles may be coated with the antigen that is complementary to the analyte or, optionally, one type of particle may be coated with the antigen and the other with a second antibody directed against the antibody analyte. In this mode, in the presence of the antibody analyte, the small polydisperse metal particles will complex with the monodisperse polymeric particles, and the abovedescribed statistical changes in the light scatter pulse height distribution histogram measured.

The foregoing has described assaying for a single analyte in a fluid sample. It is within the scope of this invention to analyze concurrently multiple analytes in the same fluid sample without the need to split the sample for multiple assays as must be done in prior art methods. This may be accomplished by assigning to each analyte to be determined a polymeric microsphere of a unique diameter and/or refractive index and a type of binding reaction. The coatings on the different size microspheres will, of course, be determined by the type of assay system to be assigned to the analyte, e.g., forward binding, inhibition, displacement or competition. The assay systems for the multiple analytes may be the same or different. This embodiment of the invention relies upon the electronic components of the FPA to monitor the light scatter signals produced by each differently sized polymeric microsphere. Electronic systems for monitoring each size of microsphere are disclosed in copending U.S. patent application Ser. No. 883,574, which is incorporated by reference. Briefly, signals from light detectors that receive the light scatter signals from polymeric microspheres may be analyzed by either of two analytical systems. In a preferred analytical system which is software based, pulses from the light scatter detector are fed to an analog-to-digital converter which samples the peak height of each pulse and passes these peak height values to a computer which sorts the peak height values by size and then arranges them in a histogram, which may be a smoothed histogram, one for each analyte.

Binding molecule-coated polymeric microspheres may be purchased commercially (Polysciences, Inc.) or prepared as described in Seaman, 1990, above. In a typical coating procedure, suspensions of microspheres are incubated with a buffered (pH 7 to 8) solution of a first binding molecule at a concentration and for a period of time (typically, 0.5 to 16 hrs) sufficient to reach equilibrium binding of the molecule to the microspheres. Coated microspheres are recovered by brief centrifugation, and nonspecific binding sites blocked by a brief (e.g. 15 min) exposure to a solution of an inert protein (e.g., nonfat dry milk solids or serum albumin). Coated microspheres are then washed at least three times with an at least 4-fold volume of cold storage buffer. Any storage buffer that provides stability to the microsphere suspensions on storage may be used. Typical storage buffers are 0.5% BSA-0.1% $NaN_3$ in 0.154M NaCl, pH 7.4, or 0.1% BSA-0.01% $NaN_3$ in 10 mM HEPES buffer, pH 7.5.

The polydisperse metal colloids may be of metals and metal compounds, such as metal oxides, metal hydroxides and metal salts. Examples include the metals gold, platinum, silver and copper; gold is highly preferred. Methods of production of colloidal gold of the desired range of particle diameters, and methods for coating metal particles with proteins, are described generally in Roth, J., "The Colloidal Gold Marker System for Light and Electron Microscopy Cytochemistry", in Bullock, G. R. et al., *Techniques in Immunochemistry*, 2: 217 (19), in Horisberger, M., *SEM* 11: 9 (1981), in Weiser, H. B., Inorganic Colloid Chemistry, J. Wiley, N.Y. 1931, p. 1, in Leuvering, J. H. W., U.S. Pat. No. 4,313,734, and in Frens, G., *Nature, Physical Science*, 241:20 (1973), all of which are incorporated by reference.

Polydisperse colloidal gold particle suspensions may be obtained from E-Y Laboratories, Inc., San Matteo, Calif. 94401 or prepared as described in the above-cited references. In a preferred method, polydisperse colloidal gold particles of particle size 10 nm to 120 nm diameter are produced by the method of Frens (1973) above. Although this method produces a relatively broad range of gold particle sizes, the dimensions of the range is not a critical factor in the present invention. As noted above, gold particles of such sizes do not produce measurable and interfering light scatter under the conditions of the invention. Within the present context, therefore, by "polydisperse metal particles" is meant a population of colloidal metal particles whose diameters range between 20 nm and 120 mm.

In one method of coating gold particles with antibody, the above-described solution of gold particle is titrated to pH 7.5 using $K_2CO_3$. The coating molecule, e.g., antibody is dissolved in 10 mM HEPES buffer, pH 7.5, containing 0.02% BSA as a stabilizer, and one-tenth volume is added to the gold particle solution. After 60 mins of mixing, a one-tenth volume of 0.1% non-fat dried milk solids is added in order to block nonspecific binding sites. The particles are washed three times by centrifugation in the storage buffer (10 mM HEPES, pH 7.5, 0.1% BSA, 0.01% $NAN_3$, 1% mannitol) and used immediately or stored at 4° C. Other methods for coating gold particles are described in Leuvering above, which is incorporated by reference.

Using the present invention, highly sensitive assays for a multi-epitopic, high molecular weight antigen such as thyroid stimulating hormone (TSH) may be carried out by either passively or covalently binding appropriately complementary polyclonal or monoclonal antibodies to the colloidal metal (e.g. gold) particles and polymeric (e.g. latex) microspheres. The exact method of protein binding is not critical provided that the immunological integrity of the protein is not compromised, and that the binding is stable under the conditions of the assay. Particularly preferred for this assay are 1.62 μm diameter latex microspheres with a CV of about 2% (Interfacial Dynamics Corp.). Colloidal gold particles with polydispersed sizes in the range of 50 to 80 nm, as determined by electron microscopy, made as described above, are particularly preferred.

As noted above, I have found that colloidal metal particles, when used at high densities relative to polymeric microspheres such as from 2 to 100,000 to 1, act as "scavengers" for nonspecific interfering substances commonly found in fluid samples of biological origin, such as human serum. That is to say, the metal particles not only provide the basis for the quantitative immunoassay of the invention, but also reduce the deleterious effects of interfering substances. Although the useful particle ratio in this regard is very broad, metal particle to polymeric microsphere ratios of the order of 1000 to 10000:1 are preferred.

The following examples are provided merely to illustrate several embodiments of the invention, and are not intended to delimit the scope of the invention which is encompassed by the specification and included claims.

EXAMPLE 1

Forward (Sandwich) Binding Reaction Assay for Serum TSH

Polydisperse colloidal gold particles (50–80nm) were coated with a first anti-TSH monoclonal antibody (BioDesign International, Inc., Kennebunkport, Me. 04046) as follows. A suspension of colloidal gold particles was brought to pH 7.5 using 0.2M potassium carbonate. To this suspension was added a 0.1 volume of the coating antibody diluted in 10 mM HEPES-0.02% BSA, pH 7.5. After mixing for 1 hr, a 0.1 volume of a solution of non-fat dried milk solids were added with mixing. The particles were washed three times by centrifugation in 10 mM HEPES buffer (pH 7.5) containing 1% BSA, 0.01% $NaN_3$ and 1% mannitol.

Polystyrene (latex) beads of 1.62 μm diameter (approximate diameter CV of 2.0%) were coated with a second anti-TSH monoclonal antibody as described in Hansen, U.S. patent application Ser. No. 883,574, which is incorporated herein by reference.

Figure 2B:
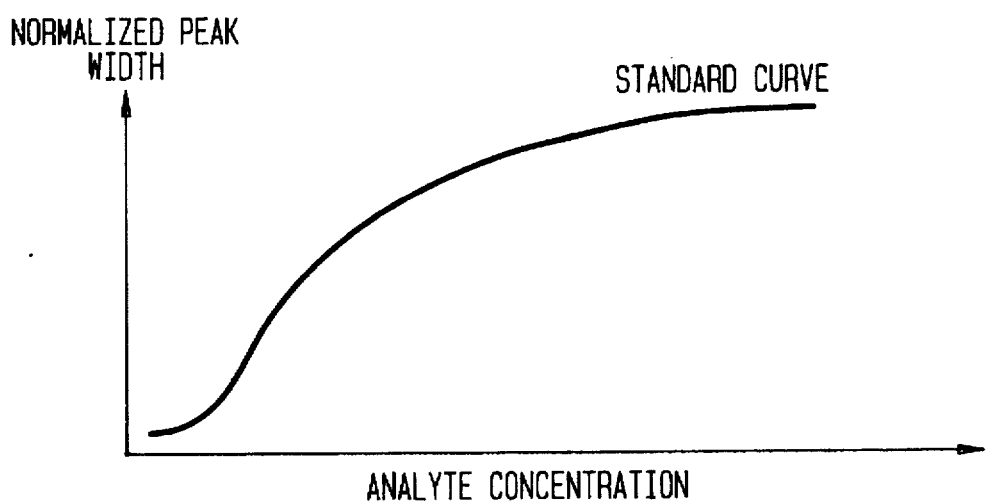
Figure 3A:
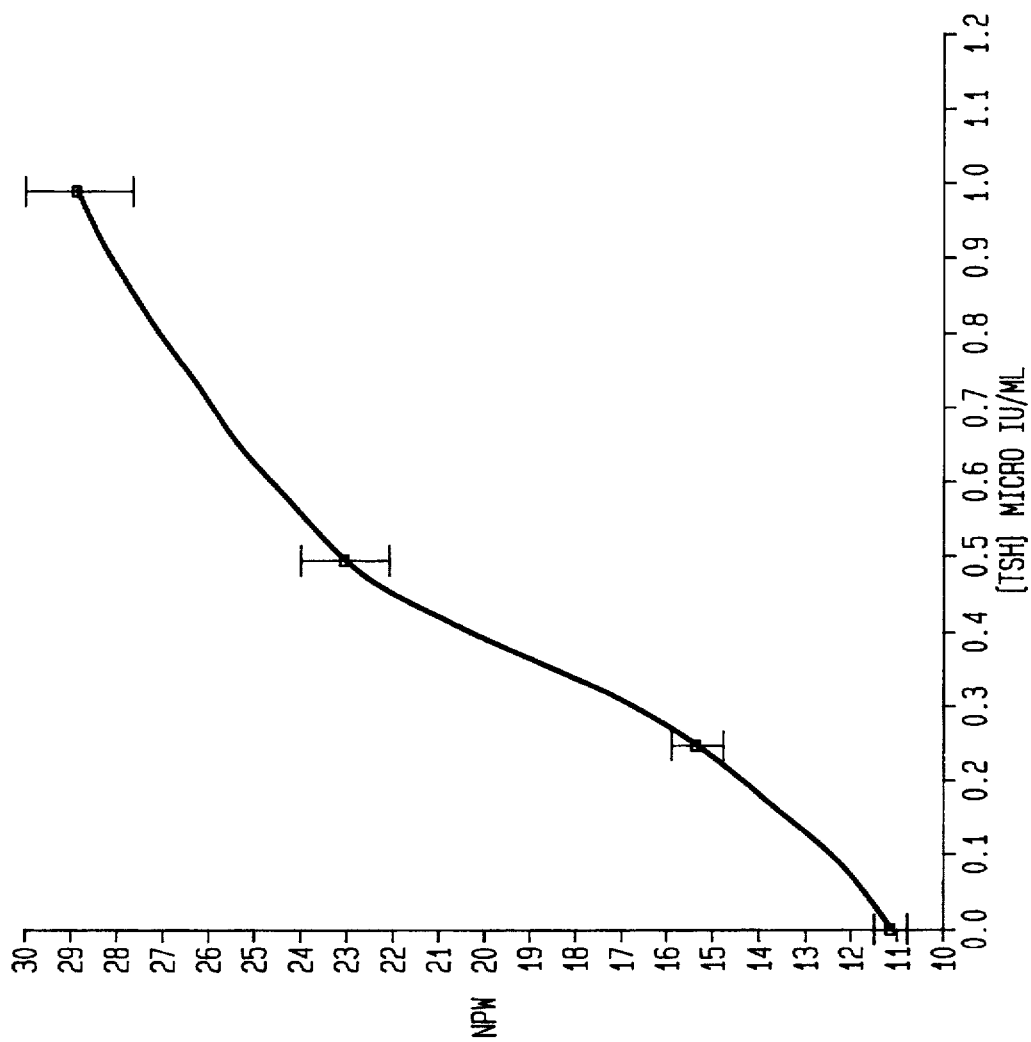
FIG. 3A shows a human serum TSH assay standard curve.
Figure 3B:
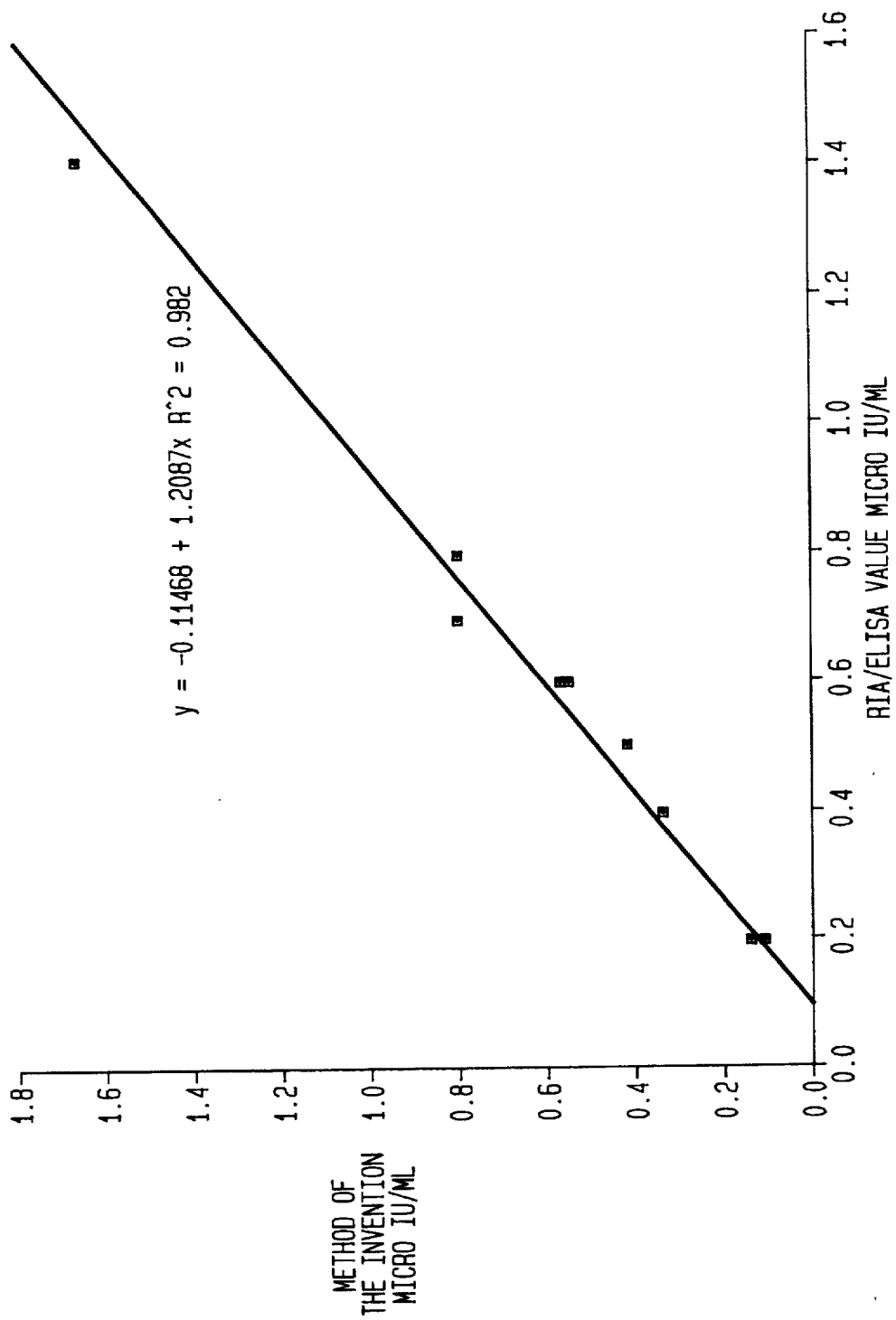
FIG. 3B shows a comparison with other methods.

Coated gold particles were mixed with coated latex particles in a ratio of 10,000 to 1 to form Reagent A. Reagent A was added to TSH-containing serum in a volume such that the final latex microsphere density was about $2\times10^6$/mL, and the serum was 40%. After 60 minutes of incubation at room temperature, the mixture was measured in a sheath FPA as described above using low angle forward light scatter. Normalized peak width units ("NPW") illustrated in FIG. 2A as a function of the number of events and in FIG. 2B as a function of analyte concentration as a function of analyte TSH concentration in the serum over the concentration range of 0 to 1.2 μIU/mL is shown in FIG. 3A. FIG. 3B illustrates a linearized interpretation of the TSH assay compared with an RIA/ELISA. The sensitivity of this assay was about $5\times10^{-13}$M in serum.

EXAMPLE 2

Inhibition assay for Thyroxine (T4)

Monodisperse latex microspheres (1.62 μm diameter, Interfacial Dynamics Corp.) were coated with human thyroglobulin (Calbiochem Inc.) as follows to form Reagent A. The microspheres were incubated overnight with antigen thyroglobulin in 10 mM HEPES buffer, pH 7.5. Microspheres, recovered by centrifugation, were washed with HEPES buffer containing BSA and $NaN_3$ as described above, and stored in the same buffer containing mannitol.

Polydisperse colloidal gold particles (50–80 nm diameter) were coated with an antibody to T4 as follows to form Reagent B. One-tenth volume of 10 mM HEPES buffer (pH 7.5) containing antibody and BSA was added to the gold particles. For the T4 assay, an IgG-purified polyclonal antibody specific to T4 (OEM Concepts) was used for coating. Coated particles were then post-coated with a solution of non-fat dry milk powder to block nonspecific binding sites. Particles were recovered by centrifugation and washed with 10 mM HEPES buffer (pH 7.5) containing BSA and $NAN_3$. Washed particles were stored to the same buffer, to which mannitol was added as a stabilizer. Coated gold particles were diluted into an assay buffer containing 50 mM glycine (pH 9), 10 mM EDTA, 0.01% aminonaphthosulfonic acid (Sigma Chem. Co., St. Louis, Mo.), 0.1% BSA, 0.3M KI and 0.01% $NAN_3$.

Serum samples containing T4 were incubated with Reagent B for 30 minutes, and then Reagent A was added to deliver a microsphere density of $2\times10^7$/mL. After an additional 30-minute incubation, samples were analyzed in the FPA for histogram peak width determination using low angle forward light scatter.

Figure 4A:
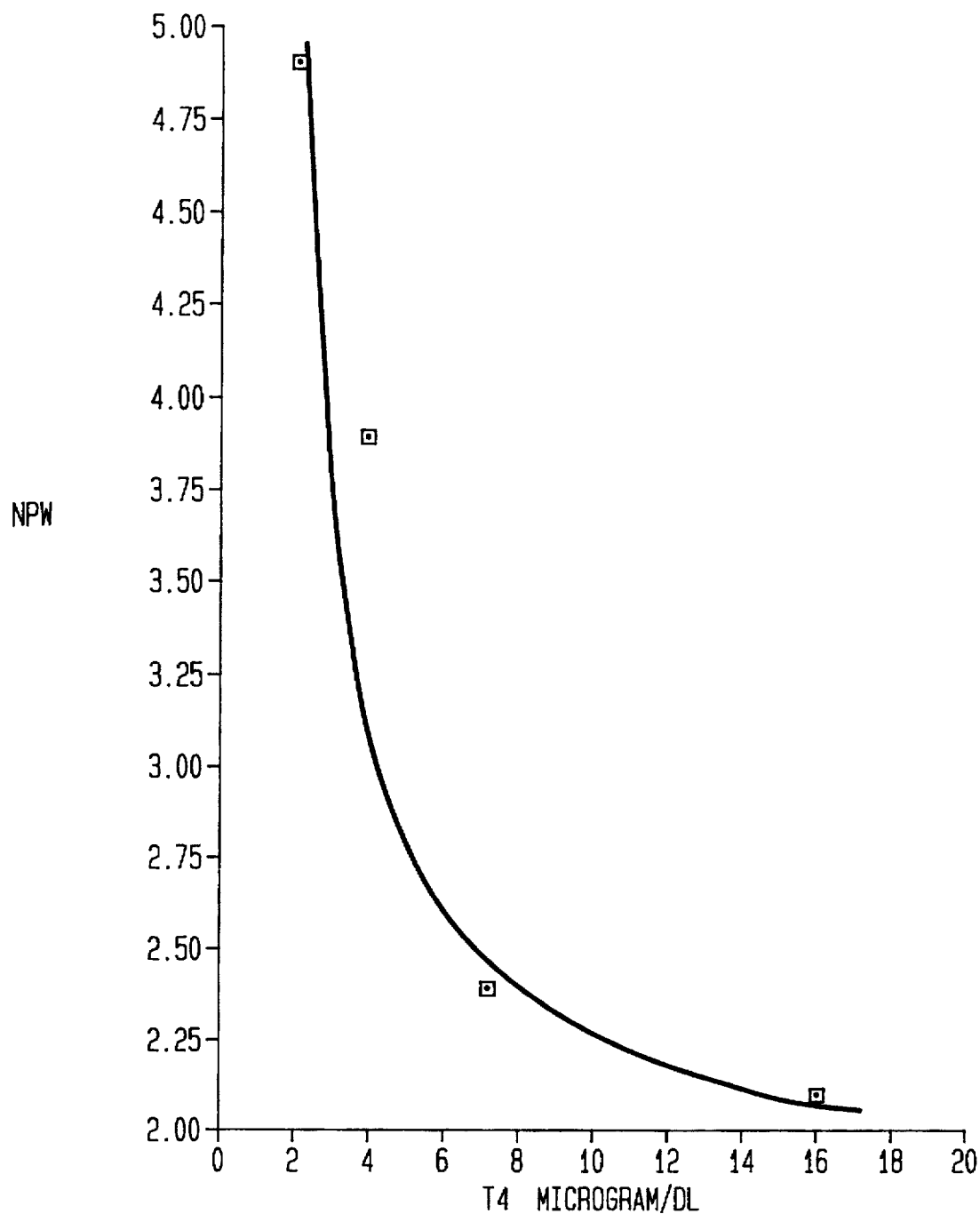
FIG. 4A shows a T4 standard curve.
Figure 4B:
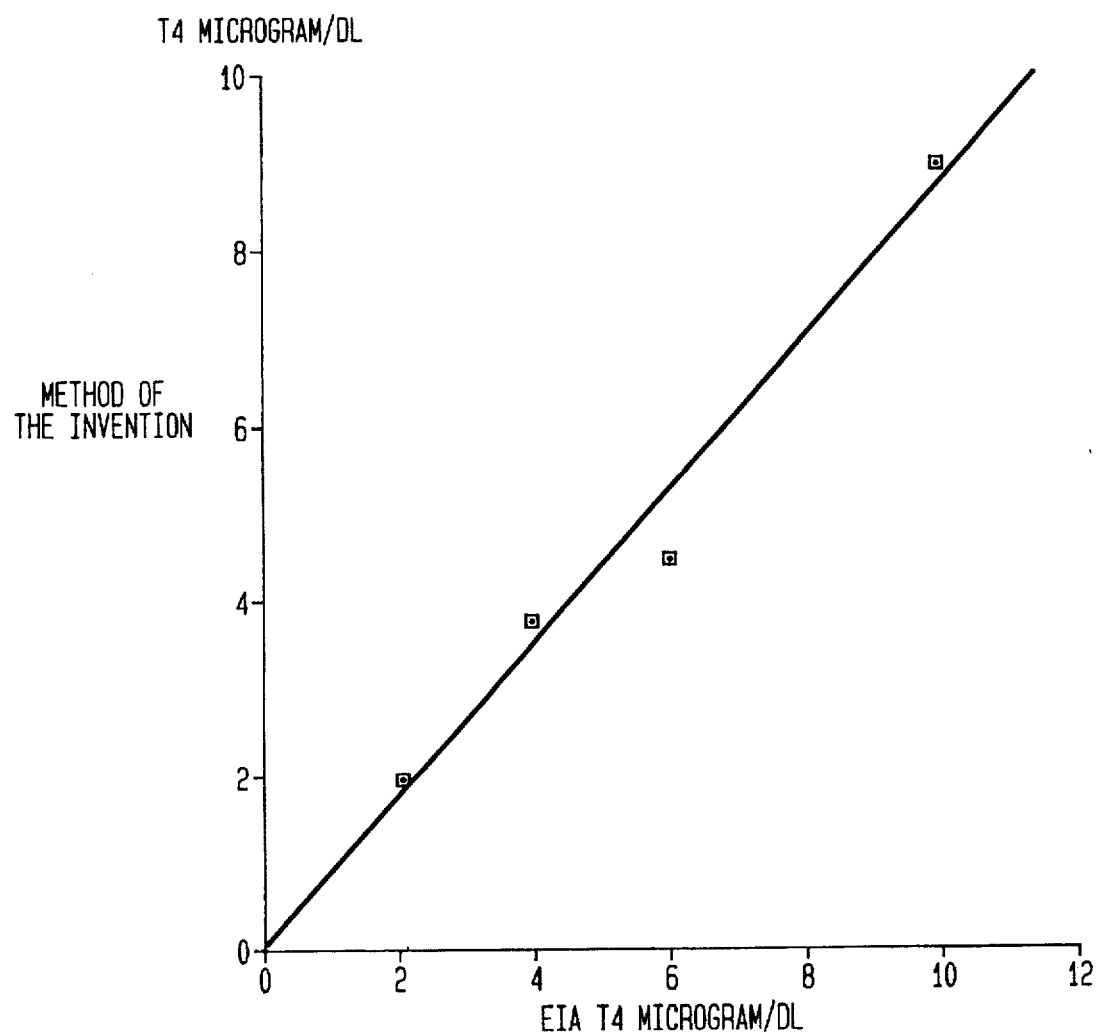
FIG. 4B shows a comparison with other methods.

Serum T4 inhibits the binding of gold particles with latex thyroglobulin. High concentrations of serum T4 produced narrow histogram peak widths, and low concentrations of serum T4 produced the converse (FIG. 4A). The curve in FIG. 4A was generated using calibrator sera (Biomerica, Inc., San Luis Obispo, Calif.) and served as the standard curve for further comparisons with standard EIA methods, i.e., the EMIT method (Syva Corp., Palo Alto, Calif.). The correlation data are shown in FIG. 4B. The correlation was >95% over the analyte concentration range shown.

EXAMPLE 3

Simultaneous Assay of TSH and T4 in The Same Fluid Sample

The TSH and T4 immunoassays described in Examples 1 and 2 were combined in order to demonstrate that multiple analytes may be analyzed in the same fluid sample. The T4 and TSH assays were carried out with monodispersed latex microsphere populations having mean diameters of 0.95 μm and 1.62 μm, respectively. The final serum concentration was 15%, the gold particle concentration was 1×10$^{10}$/mL, and the latex microsphere concentrations were 1×10$^8$/mL for T4 and 5×10$^6$/mL for TSH.

Reactions were carried out in the following sequence. The TSH-assay reaction was performed as described in Example 1. After 30 minutes of this reaction, Reagent B of Example 2 was added. Twenty-five minutes thereafter, Reagent A of Example 2 was added and the mixture incubated for five minutes. FPA analysis was then performed.

When midrange concentrations of the analytes were assayed with the FPA system and methods of the present invention, the results were 4 μg/mL for T4 and 2 μIU/ml for TSH. When a sample with no T4 and a TSH midrange level of 2 μIU/mL was assayed by the present method, the measured T4 value was zero, and the measured value for TSH was 2 μIU/mL±10%. With a sample with a known low value for TSH (0.3 μIU/mL) and a known midrange value of 4 μg/mL for T4, the present method correlated within 10% with the known values.

This experiment demonstrates the way in which the present invention permits simultaneous assays can be performed with separable results, and with no detectable cross-interference between assays in a single run.

EXAMPLE 4

Comparison of The Present Method With a Standard Latex-Latex Agglutination Method for IgE Determination In order to demonstrate the efficacy of the present invention in suppressing the adverse effects of non-specific binding, an assay for human IgE was conducted in two formats. In the first format, ordinary latex microsphere-latex microsphere agglutination was carried out with anti-IgE polyclonal antibodies passively coated on the latex particles, according to the method of Masson et al., above, in which the disappearance of monomeric particles is monitored. The latex particle diameter was 1.62 μm. The second format consisted of the forward binding reaction embodiment of the present invention.

To coat gold particles, a suspension of gold particles was titrated to pH 7.5 with 0.2M $K_2CO_3$. To this suspension was added a one-tenth volume of mouse monoclonal anti-human IgE (Biodesign International, Inc., Kennebunkport, Me., 04046) in 10 mM HEPES buffer, pH 7.5, containing 0.02% BSA. After 60 minutes of mixing, a one-tenth volume of 0.1% non-fat dried milk solids solution was added. The particles were isolated by centrifugation washed three times with the same buffer, then stored in a storage buffer consisting of 10 mM HEPES, 0.01% BSA, 0.01% $NAN_3$, 1% mannitol.

To coat latex microspheres, 1.62 μm latex microspheres (Interfacial Dynamics Intnl., Portland, Oreg. 97220) were diluted to a density of 0.5% in 10 mM HEPES, pH 7.5, the suspension was incubated overnight at 4° C. with a 100 μg/mL solution of affinity-purified goat anti-human IgE, microspheres were isolated by centrifugation and washed three time with HEPES buffer, and finally stored in 10 mM HEPES, 0.1% BSA, 0.01% $NAN_3$, 1% mannitol.

For assay, latex and gold particles were diluted to 1×10$^8$/mL and 2×10$^{10}$/mL respectively, in assay buffer. A 50 μl aliquot of analyte serum sample was added to 450 μl of the particle mixture, and mixed by vortexing; the final serum dilution was 10%. After 15 minutes of incubation at 23° C., the reaction mixture was subjected to FPA analysis. The assay buffer was 0.05M glycine 0.1% BSA, 0.3M KI, 0.01% $NAN_3$, pH 9.5.

A commercial ELISA IgE assay method for serum IgE(Ventrex Laboratories, Portland, ME) served as the reference standard for both formats. The correlation curve for the latex-latex agglutination format is shown in FIG. 5A and that for the method of the invention in FIG. 5B. It is clear from the data that the correlation is poor and that the sensitivity is limited for the latex agglutination method, likely due to the influence of interfering substances in the analyte serum sample. In sharp contrast, the latex microsphere-gold particle method of the present invention shows an excellent correlation with the reference method (FIG. 5B).

EXAMPLE 5

Kinetics of Histogram Peak Width Broadening

The assay of Example 1 was carried out in a manner that permitted low angle forward light scatter FPA analyses of the reaction mixture (containing 6 μIU/mL TSH) at intervals.

Figure 6:
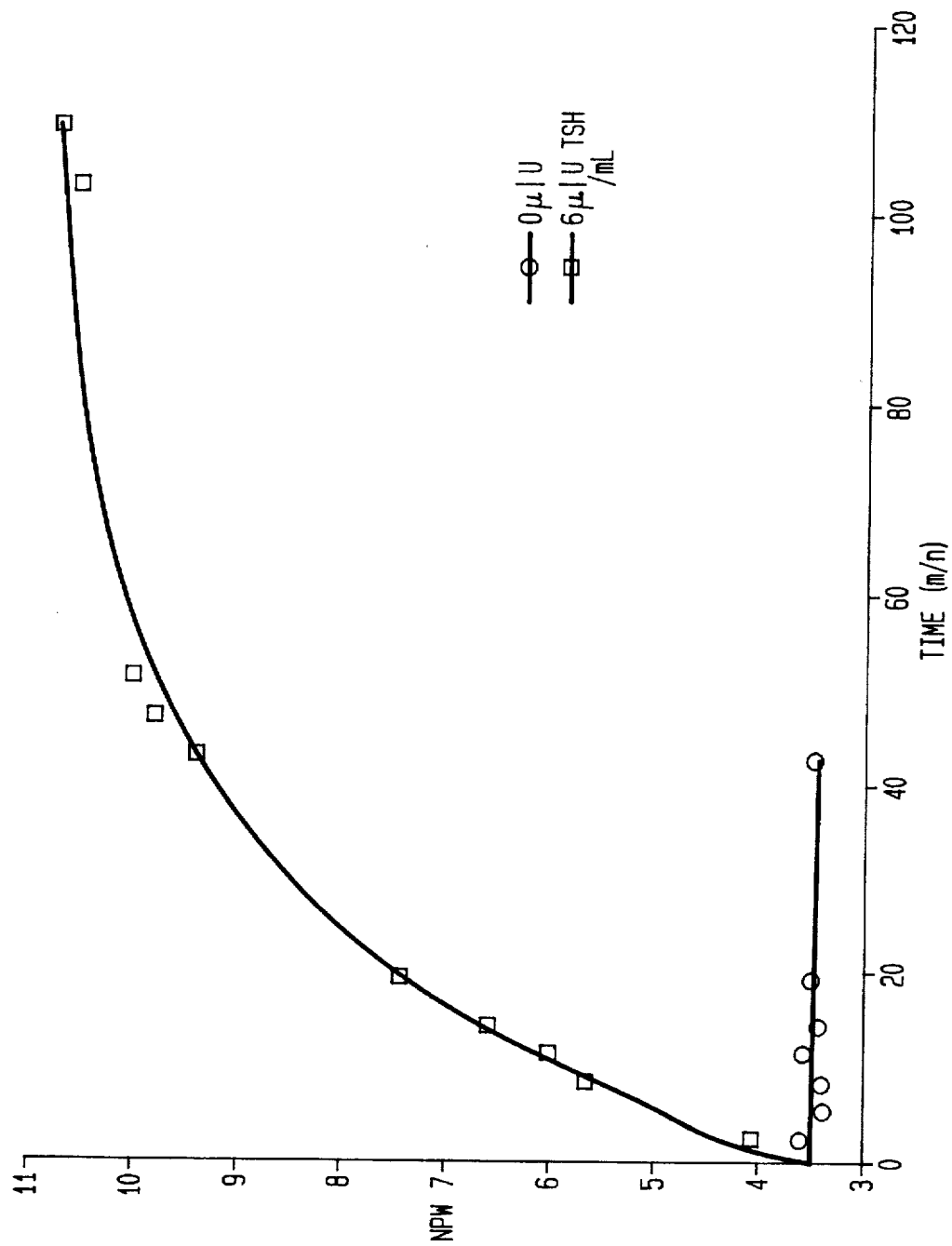
FIG. 6 shows the kinetics of binding of colloidal gold particles to latex microspheres brought about by analyte.

In the absence of analyte (—o—, FIG. 6), coated gold particles did not bind to coated latex microspheres, and there was no change in histogram dimension. However, in the presence of analyte (—□—, in FIG. 6) binding was detected from the first time point (2 min.), as reflected by a broadening of the histogram derived from the monodisperse latex microspheres. This broadening continued at a linear rate for the first 20 minutes of reaction, and reached a plateau at about 100 minutes.

I claim:

1. A particle light scatter-based immunoassay for measuring an analyte in a fluid sample, comprising the steps of:

a) combining with said fluid sample a reagent set including first binding molecule-coated monodisperse microspheres and second binding molecule-coated colloidal metal particles smaller than said microspheres or an immunocomplex comprising said monodisperse microspheres and said colloidal metal particles, to form a mixture and allow a reaction to occur, wherein at least one of said first and second binding molecules binds said analyte, said reaction being formation or decomplexation of said immunocomplex, so that the reacted mixture includes said microspheres in uncomplexed form, in said immunocomplex or both, the degree of binding of said microspheres in said reacted mixture with said colloidal metal particles being dependent upon presence or amount of said analyte in said fluid sample;

b) measuring light scattered by said microspheres in said reacted mixture by means of an optical flow particle analyzer to thereby provide light scatter signals for said microspheres;

c) determining a dimension of a statistical distribution of said light scatter signals from said microspheres in said reacted mixture, such that the dimension of said statistical distribution varies with the degree of binding of said microspheres with said colloidal metal particles in said reacted mixture; and d) correlating said dimension of said statistical distribution of said light scatter signals for said microspheres in said reacted mixture with the amount of said analyte in said fluid sample.

2. A method according to claim 1, wherein said second binding-molecule coated colloidal metal particles are polydisperse colloidal metal particles.

3. A particle light scatter-based immunoassay for measuring an analyte in a fluid sample, comprising the steps of:
   a) combining with said fluid sample a reagent set including first binding molecule-coated polymeric monodisperse microspheres and second binding molecule-coated colloidal metallic particles smaller than said microspheres or an immunocomplex comprising said monodisperse microspheres and said colloidal metal particles, to form a mixture and allow a reaction to occur, wherein at least one of said first and second binding molecules binds said analyte, said reaction being formation or decomplexation of said immunocomplex, so that the reacted mixture includes said microspheres in uncomplexed form, in said immunocomplex or both, the degree of binding of said microspheres in said reacted mixture with said colloidal metal particles being dependent upon presence or amount of analyte in said fluid sample;
   b) measuring light scattered by said microspheres in said reacted mixture by means of an optical flow particle analyzer to thereby provide light scatter signals for said microspheres;
   c) determining a dimension of a statistical distribution in the form of a histogram of pulse heights of said light scatter signals for said microspheres in said reacted mixture, wherein said histogram of pulse heights for said microspheres does not overlap with a histogram of pulse heights for said colloidal metal particles, such that the dimension of said histogram varies with the degree of binding of said microspheres with said colloidal metal particles in said reacted mixture; and
   d) correlating said dimension of said histogram of said light scatter signals for said microspheres in said reacted mixture with the amount of said analyte in said fluid sample.

4. A method according to claim 3, further comprising the steps of measuring light scatter signals for a control mixture including said microspheres in said optical flow particle analyzer, determining said dimension of said histogram of said light scatter signals form microspheres in said control mixture, said step of correlating said dimension of said histogram of said light scatter signals from said microsphere in said reacted mixture including the step of comparing such dimension with the dimension of said histogram of said light scatter signals from microspheres in said control mixture to determine the change in said dimension of caused by the reaction.

5. A method according to any one of claims 1–3, wherein said light scatter signals are substantially low angle forward light scatter signals.

6. A method according to any one of claims 1–3, wherein said light scatter signals are substantially right angle light scatter signals.

7. A method according to claim 3, wherein the binding of said second binding molecule-coated colloidal particles to said first binding molecule-coated polymeric microspheres is increased by said analyte, and said increase results in an increase in said dimension of said histogram.

8. A method according to claim 3, wherein the binding of said second binding molecule-coated colloidal particles to said first binding molecule-coated polymeric microspheres is decreased by said analyte, and said decrease results in a decrease in said dimension of said histogram.

9. A method according to claim 3, wherein said histogram dimension comprises a normalized peak width of a graphical representation of said histogram.

10. A method according to any one of claims 1–3, further comprising the step of providing a ratio of said metal particles to said polymeric microspheres effective to reduce interference in said immunoassay by nonspecific binding substances.

11. A method of claim 10, wherein said ratio ranges between 2 and 100,000 to 1.

12. A method of claim 10, wherein said ratio ranges between 1,000 and 10,000 to 1.

13. A method according to any one of claims 1–3, wherein said monodisperse microspheres comprise uniform polymeric microspheres.

14. A method according to any one of claims 1–3, wherein said microspheres comprise microspheres having an average diameter ranging between about 0.02 and about 100 μm.

15. A method according to any one of claims 1–3, wherein said microspheres comprise microspheres having an average diameter ranging between about 0.05 and about 10.0 μm.

16. A method according to any one of claims 1–3, wherein said microspheres comprise microspheres having an average diameter ranging between about 0.5 and about 5.0 μm.

17. A method according to any one of claims 1–3, wherein said colloidal metal particles are selected from the group consisting of gold, platinum, silver and copper particles.

18. A method according to any one of claims 1–3, wherein said colloidal metal particles are gold particles.

19. A method according to any one of claim 1–3, wherein the average diameter of said metal particles ranges between about 20 nm and about 120 nm.

20. A method according to any one of claims 1–3, wherein the average diameter of said metal particles ranges between about 50 nm and about 80 nm.

21. A method according to any one of claims 1–3, wherein the ratio of the average diameter of said microspheres to the average diameter of said metal particles is between about 15:1 and about 30:1.

22. A method according to claim 4, wherein said microspheres in said control mixture are non-immunochemically sensitized monodisperse polymeric microspheres, and wherein said step of measuring the light scatter signals in an optical flow particle analyzer includes the step of regulating the diameter of a sample stream of said mixture in said analzyer to within ranges between about 3 μm and 10 μm so as to produce a coefficient of variation of said light scatter signals around a graphical representation of a histogram mean of no greater than about 2% for said non-immunochemically sensitized monodisperse polymeric microspheres in said control mixture.

23. A method according to any one of claims 1–3 wherein said step of combining said reagent set with said fluid sample includes the steps of combining said second binding molecule coated colloidal metal particles with said fluid sample to form a first mixture and incubating said first mixture so that said second binding molecule coated colloidal metal particles bind said analyte and so that the amount of unbound colloidal metal particles in said first mixture is inversely related to the amount of analyte in said fluid sample, and then combining said first mixture with said first binding molecule coated microspheres to form said reacted mixture.

24. A method according to any one of claims 1–3 wherein said fluid sample includes a plurality of analytes, said combining step includes the step of providing a separate reagent set for each said analyte and combining all of said reagent sets with said fluid sample so that said reacted mixture includes microspheres from all of said reagent sets, said measuring step including the step of measuring said light scatter signals for all of said microspheres, the microspheres in each said reagent set having a diameter or refractive index different from the microspheres in each other reagent set, and said step of determining a dimension of a statistical distribution of said light scatter signals including the step of separating light scatter signals representing microspheres from different reagent sets to form a separate statistical distribution associated with each analyte and determining a dimension for each separate distribution.

25. A method for detecting an analyte in a fluid sample by analyte-mediated binding reaction comprising the steps of:
    a) placing in a reaction vessel monodisperse polymeric microspheres coated with a first binding molecule which binds said analyte, polydisperse colloidal metal particles coated with a second binding molecule which binds said analyte and a fluid sample containing said analyte for a period of time effective to form a reacted mixture including immunocomplexes among the three components whereby at least some of said microspheres will be incorporated in said immunocomplexes;
    b) measuring light scattered by said microspheres in said reacted mixture including said microspheres in said immunocomplexes by means of an optical flow particle analyzer to thereby provide light scatter signals for said microspheres; and
    c) measuring the dimensions of the pulse height distribution histogram of said light scatter signals,
    d) comparing said dimensions in c) with the dimensions for a control mixture composed of monodisperse polymeric microspheres analyzed in the absence of analyte or colloidal metal particles, to determine the change in said histogram dimension in c); and,
    e) relating said change in said histogram dimension to the concentration of said analyte in said fluid sample.

26. A method according to claim 25, wherein said analyte is an antigen or hapten, said first binding molecule comprises a first anti-analyte antibody, and said second binding molecule comprises a second anti-analyte antibody.

27. A method according to claim 25, wherein said analyte is an antibody, and said first and said second binding molecules are each an antigen or hapten which binds said analyte antibody, or wherein said first binding molecule comprises an antigen which binds said analyte antibody and said second binding molecule comprises an antibody specific to said analyte antibody.

28. A method of detecting an analyte in a fluid sample by analyte-mediated displacement reaction comprising the steps of:
    a) providing an immunocomplex reagent including analyte-coated monodisperse polymeric microspheres and polydisperse colloidal metal particles coated with a binding molecule which binds said analyte or analyte-coated colloidal metal particles and polymeric microspheres coated with a binding molecule which binds said analyte;
    b) mixing said immunocomplex reagent with a fluid sample containing said analyte for a period of time sufficient for said analyte to displace a portion of said colloidal metal particles from said immunocomplex;
    c) measuring light scattered by said microspheres both before and after displacement with analyte in step b) by means of an optical flow particle analyzer to thereby provide light scatter signals for said microspheres;
    d) determining a dimension of the pulse height distribution histograms of said light scatter signals for said microspheres both before and after displacement with analyte in step b) to thereby determine the change in such dimension; and
    e) relating the changes in said histogram dimensions to the concentration of said analyte in said fluid sample.

29. A method according to claim 28, wherein said analyte is an antigen or hapten.

30. A method according to claim 28, wherein said analyte is an antibody, and said binding molecule is the corresponding antigen.

31. A method for detecting an antigen or hapten analyte in a fluid sample by a competition reaction comprising the steps of:
    a) mixing anti-analyte antibody-coated polydisperse metal particles, analyte, antigen or hapten-coated monodisperse polymeric microspheres, and a fluid sample containing analyte antigen or hapten to form a mixture and holding said mixture for a period of time sufficient for competition immunocomplexes to form in said mixture whereby at least some of said microspheres will be incorporated in said immunocomplexes;
    b) measuring light scattered by said microspheres in said mixture before and after formation of said competition immunocomplexes, by means of an optical flow particle analyzer to thereby provide light scatter signals for said microspheres;
    c) determining a dimension of the pulse height distribution histograms for said light scatter signals before and after said competition immunocomplex formation; and
    d) relating the change in said histogram dimension to the concentration of said analyte in said fluid sample.

32. A method for detecting an analyte antibody in a fluid sample by a competition reaction comprising the steps of:
    a) mixing polydisperse metal particles coated with antigen or hapten which binds to an analyte antibody, a fluid sample containing the analyte antibody, and monodisperse polymeric microspheres coated with a binding molecule which binds said antigen or hapten to form a mixture and holding said reacted mixture for a period of time sufficient for competition immunocomplexes to form;
    b) measuring light scattered by said microspheres in said reacted mixture before and after formation of said competition immunocomplexes by means of an optical flow particle analyzer to thereby provide light scatter signals for said microspheres,
    c) determining a dimension of the light scatter pulse height distribution histograms for said light scatter signals before and after said competition immunocomplex formation; and
    d) relating the changes in said histogram dimension to the concentration of said analyte in said fluid sample.

33. A method for detecting an analyte in a fluid sample consisting of an inhibition reaction, comprising the steps of:
    a) providing monodisperse polymeric microspheres coated with a first binding molecule that is conjugated to analyte to form a first reagent;
    b) providing polydisperse metal particles coated with a second binding molecule which binds analyte to form a second reagent;
    c) combining an analyte-containing fluid sample with said second reagent to form a first mixture and incubating said first mixture for a period of time sufficient to form a first immunocomplex incorporating said metal particles and leaving some unbound metal particles such that the amount of unbound metal particles in said first mixture is inversely related to the concentration of analyte in said sample;

d) combining said first mixture with said first reagent to form a second mixture, and incubating said second mixture to form a second immunocomplex between said microspheres said unbound metal particles;

e) measuring light scattered by said microspheres in said second mixture by means of an optical flow particle analyzer to thereby provide light scatter signals for said microspheres; and f) measuring a dimension of the pulse height distribution histogram of said light scatter signals;

g) comparing said dimensions in f) with the same dimension for a control reaction mixture composed of coated monodisperse polymeric microspheres in the absence of analyte or metal particles to determine the statistical change in said histogram dimension in f); and h) relating the change in said histogram dimension to the concentration of said analyte in said fluid sample.

34. A method according to claim 33, wherein said analyte is a hapten or antigen and said second binding molecule is an anti-hapten or anti-antigen antibody.

35. A method according to claim 33, wherein said analyte is an antibody and said second binding molecule binds said antibody.

36. A method according to any one of claims 25–35, wherein said histogram dimension is the normalized peak width of a graphical representation of said histogram.

* * * * *

UNITED STATES PATENT AND TRADEMARK OFFICE
CERTIFICATE OF CORRECTION

PATENT NO. : 5,589,401
DATED : December 31, 1996
INVENTOR(S) : Hansen et al.

It is certified that error appears in the above-indentified patent and that said Letters Patent is hereby corrected as shown below:

Column 5, line 1, delete "a"

Column 9, line 61, "abovedescribed" should read --above described--

Column 10, line 67, "mm" should read --nm--

Column 12, line 9, please insert --and individual pulse height,-- immediately after "events"

Column 13, line 24, please delete "can"

Column 13, line 63, "time" should read --times--

Column 14, line 5, "NAN$_3$," should read --NaN$_3$,--

Column 15, line 44, "form" should read --from--

Signed and Sealed this

Twenty-seventh Day of May, 1997

Attest:

BRUCE LEHMAN

Attesting Officer

Commissioner of Patents and Trademarks

UNITED STATES PATENT AND TRADEMARK OFFICE
CERTIFICATE OF CORRECTION

PATENT NO. : 5,589,401
DATED : December 31, 1996
INVENTOR(S) : Hansen et al.

It is certified that error appears in the above-identified patent and that said Letters Patent is hereby corrected as shown below:

On title page, add the following, item [73]

--Assignee: Sienna Biotech, Inc., New York, New York--

Signed and Sealed this

Ninth Day of September, 1997

Attest:

BRUCE LEHMAN

Attesting Officer

Commissioner of Patents and Trademarks